(12) United States Patent
Richard

(10) Patent No.: US 8,574,153 B2
(45) Date of Patent: Nov. 5, 2013

(54) FLEXIBLE PORT SEAL

(75) Inventor: Paul D. Richard, Shelton, CT (US)

(73) Assignee: Covidien LP, Mansfield, MA (US)

( * ) Notice: Subject to any disclaimer, the term of this patent is extended or adjusted under 35 U.S.C. 154(b) by 243 days.

(21) Appl. No.: 12/706,043

(22) Filed: Feb. 16, 2010

(65) Prior Publication Data

US 2010/0240960 A1    Sep. 23, 2010

Related U.S. Application Data

(60) Provisional application No. 61/161,833, filed on Mar. 20, 2009.

(51) Int. Cl.
*A61B 1/32*    (2006.01)

(52) U.S. Cl.
USPC ............ 600/206; 600/205; 600/207; 600/208

(58) Field of Classification Search
USPC .................. 600/201–220, 221–235, 245, 246
See application file for complete search history.

(56) References Cited

U.S. PATENT DOCUMENTS

| | | |
|---|---|---|
| 4,183,357 A | 1/1980 | Bentley et al. |
| 5,314,417 A | 5/1994 | Stephens et al. |
| 5,366,478 A | 11/1994 | Brinkerhoff et al. |
| 5,375,588 A | 12/1994 | Yoon |
| 5,391,156 A | 2/1995 | Hildwein et al. |
| 5,507,758 A | 4/1996 | Thomason et al. |
| 5,514,133 A | 5/1996 | Golub |
| 5,545,150 A | 8/1996 | Danks et al. |
| 5,634,911 A | 6/1997 | Hermann et al. |
| 5,683,378 A | 11/1997 | Christy |
| 5,842,971 A | 12/1998 | Yoon |
| 5,906,577 A | 5/1999 | Beane et al. |
| 5,964,781 A | 10/1999 | Mollenauer et al. |
| 5,997,515 A | 12/1999 | de la Torre et al. |
| 6,142,936 A | 11/2000 | Beane et al. |
| 6,228,063 B1 | 5/2001 | Aboul-Hosn |
| 6,238,373 B1 | 5/2001 | de la Torre et al. |

(Continued)

FOREIGN PATENT DOCUMENTS

| | | |
|---|---|---|
| EP | 1 774 918 A1 | 4/2007 |
| WO | WO 96/36283 | 11/1996 |

(Continued)

OTHER PUBLICATIONS

European Search Report for EP10 25 0885—completion date Aug. 18, 2010—which application corresponds to U.S. Appl. No. 12/754,638, filed Apr. 6, 2010.

(Continued)

*Primary Examiner* — Jan Christopher Merene

(57) ABSTRACT

A flexible port seal is provided for use in single incision surgery and includes an outer seal defining a bore extending from a proximal end of the outer seal to a distal end of the outer seal. A support plate is located within the bore of the outer seal and one or more throughports are attached to the support plate for receipt of a surgical instrument. The throughports form a fluid tight seal with cannulas and/or surgical instruments inserted through the throughports. The flexible port seal is formed of a compressible or flexible material to facilitate insertion through the single incision in the patient and allow for movement of the surgical instruments relative to the seal to independently orient each of the surgical instruments.

19 Claims, 7 Drawing Sheets

(56) References Cited

U.S. PATENT DOCUMENTS

| | | | |
|---|---|---|---|
| 6,382,211 B1 | 5/2002 | Crook | |
| 6,440,063 B1 | 8/2002 | Beane et al. | |
| 6,454,783 B1 | 9/2002 | Piskun | |
| 6,551,270 B1 | 4/2003 | Bimbo et al. | |
| 6,716,201 B2 | 4/2004 | Blanco | |
| 6,830,578 B2 | 12/2004 | O'Heeron et al. | |
| 6,884,253 B1 | 4/2005 | McFarlane | |
| 6,991,602 B2 | 1/2006 | Nakazawa et al. | |
| 7,163,510 B2 | 1/2007 | Kahle et al. | |
| 7,223,257 B2 | 5/2007 | Shubayev et al. | |
| 7,344,547 B2 | 3/2008 | Piskun | |
| 7,473,221 B2 | 1/2009 | Ewers et al. | |
| 7,650,887 B2 | 1/2010 | Nguyen et al. | |
| 7,798,898 B2 | 9/2010 | Luciano, Jr. et al. | |
| 7,850,600 B1* | 12/2010 | Piskun | 600/114 |
| 2002/0183594 A1 | 12/2002 | Beane | |
| 2005/0020884 A1 | 1/2005 | Hart et al. | |
| 2005/0096695 A1 | 5/2005 | Olich | |
| 2006/0224164 A1* | 10/2006 | Hart et al. | 606/108 |
| 2006/0241651 A1 | 10/2006 | Wilk | |
| 2006/0247499 A1 | 11/2006 | Butler et al. | |
| 2006/0247500 A1* | 11/2006 | Voegele et al. | 600/208 |
| 2008/0027476 A1 | 1/2008 | Piskun | |
| 2008/0255519 A1* | 10/2008 | Piskun et al. | 604/174 |
| 2009/0036745 A1* | 2/2009 | Bonadio et al. | 600/208 |
| 2009/0093752 A1 | 4/2009 | Richard et al. | |
| 2009/0227843 A1* | 9/2009 | Smith et al. | 600/208 |
| 2009/0270685 A1* | 10/2009 | Moreno et al. | 600/203 |
| 2009/0326332 A1 | 12/2009 | Carter | |
| 2010/0113886 A1* | 5/2010 | Piskun et al. | 600/231 |
| 2010/0217087 A1* | 8/2010 | Bonadio et al. | 600/205 |
| 2010/0249516 A1* | 9/2010 | Shelton et al. | 600/203 |
| 2010/0298646 A1* | 11/2010 | Stellon et al. | 600/208 |
| 2010/0312063 A1* | 12/2010 | Hess et al. | 600/204 |
| 2011/0112371 A1* | 5/2011 | Smith et al. | 600/201 |

FOREIGN PATENT DOCUMENTS

| | | |
|---|---|---|
| WO | WO 97/33520 | 9/1997 |
| WO | WO 01/49363 A1 | 7/2001 |
| WO | WO2006/019723 A2 | 2/2006 |
| WO | WO2006/110733 A2 | 10/2006 |
| WO | WO 2008/093313 A1 | 8/2008 |
| WO | WO2008/121294 A1 | 10/2008 |

OTHER PUBLICATIONS

European Search Report (2 pages) for coresponding EP10252526—date of completion Jun. 23, 2010.

* cited by examiner

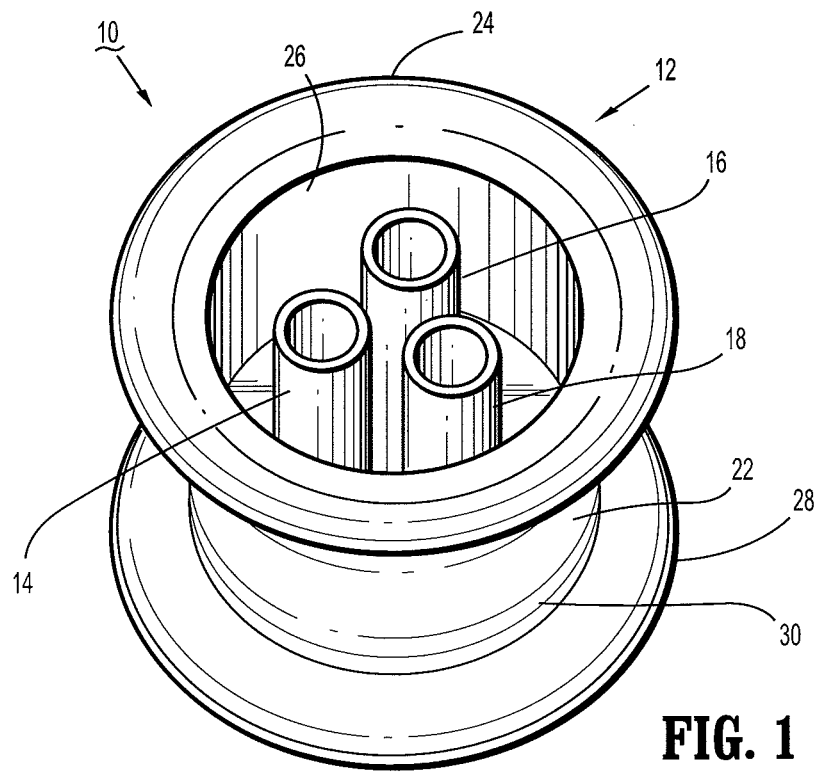
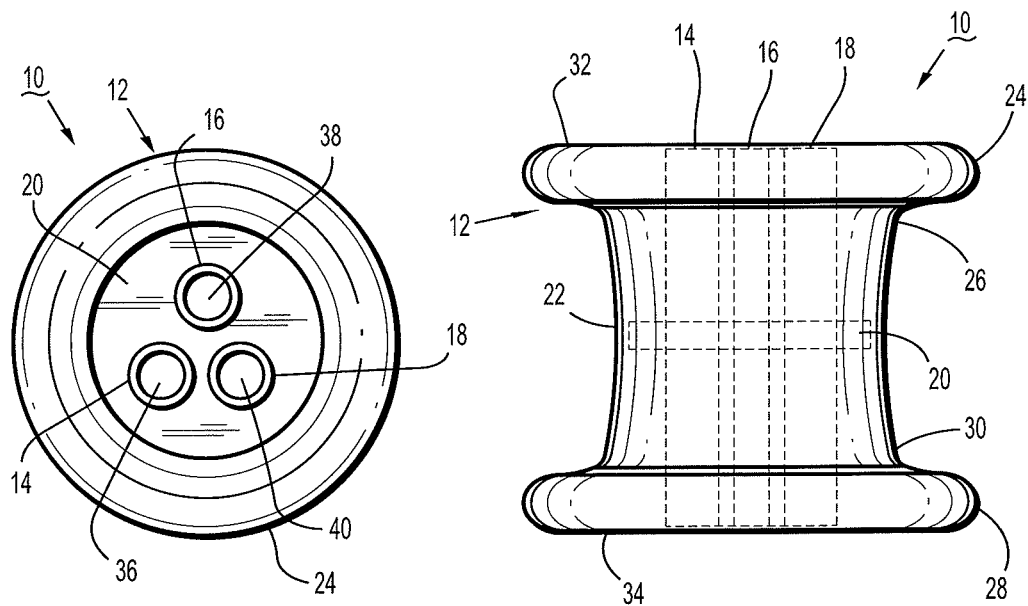
FIG. 1
FIG. 2
FIG. 3

FLEXIBLE PORT SEAL

CROSS REFERENCE TO RELATED APPLICATION

The present application claims the benefit of and priority to U.S. Provisional Application Ser. No. 61/161,833 filed on Mar. 20, 2009, the entire contents of which are incorporated herein by reference.

BACKGROUND

1. Technical Field

The present disclosure relates to a flexible port seal for use in single incision surgical procedures. More particularly, the present disclosure relates to a flexible port seal having multiple, independently movable throughports.

2. Background of Related Art

Methods and apparatus for performing closed surgical procedures are known. Such procedures greatly reduce postoperative recovery time and minimize scarring to the patient. These procedures typically involve inserting one or more access assemblies through the abdominal wall of the patient and insufflating the abdominal cavity. A laparoscope or other viewing instrument is inserted through one of the access assemblies, or directly through the abdominal wall, to provide the clinician with an image of the abdominal cavity. The surgeon is then able to perform the procedure within the abdominal cavity by manipulating instruments that have been extended through the access assemblies.

The number and type of instruments that a surgeon may use to complete a closed procedure is limited by the number, size and configuration of the access assemblies that have been inserted into the abdominal cavity. Because traditional access assemblies are configured to provide access for only a single instrument, the simultaneous use of any additional instruments requires a corresponding access assembly. For each additional access assembly necessary to complete the procedure, an additional incision must be created. Each additional incision increases the length of the procedure and may prolong post-operative recovery time.

Therefore, it is desirable to provide an access assembly for insertion through a single incision in the body of a patient which provides multiple ports for receipt of one or more surgical instruments.

SUMMARY

There is disclosed a flexible port seal for insertion through tissue. The flexible port seal generally includes an outer seal having a proximal end and a distal end and defines a bore extending from the proximal end of the outer seal to the distal end of the outer seal. A support plate is located within the bore of the outer seal and a throughport extends through the support plate. The throughport defines a bore for receipt of a surgical instrument such that the throughport forms a fluid tight seal against a surgical instrument inserted through the throughport. In an embodiment, the surgical instrument inserted through the throughport is a cannula. Such a cannula may be configured to receive other instrumentation therethrough, e.g., clip appliers, graspers, dissectors, retractors, staplers, laser probes, photogenic devices, endoscopes and laparoscopes, tubes and the like. Alternatively, the throughport may be configured to receive such other instruments directly therethrough, e.g., without requiring a cannula to be inserted first. For the purposes of this application, the terms "instruments or instrumentation" will refer to collectively to a cannula or any of the other types of instrumentation.

The outer seal has a central portion and an upper rim at a proximal end of the central portion. The outer seal also has a lower rim at a distal end of the central portion. The upper and lower rims have a diameter greater than the diameter of the central portion.

In an embodiment, the outer seal has a groove formed in an inner surface of the outer seal for receipt of the support plate. An outer edge of the support plate is positioned within the groove formed in the inner surface of the outer seal. In a specific embodiment, the support plate is a circular disk. In an alternative embodiment, the support plate is formed integrally with the outer seal.

The support plate may include an opening such that an outer surface of the throughport forms a fluid tight seal with the opening when the throughport is positioned through the opening. Alternatively, the support plate, the outer seal and the throughport are all formed integrally with each other.

In an embodiment, the throughport is a hollow tube extending through the support plate. The throughport may include an instrument seal located within a bore of the hollow tube. In one specific embodiment, the instrument seal is an hourglass seal. In an alternative specific embodiment, the instrument seal is a duckbill valve.

In various specific embodiments, the outer seal is formed of a flexible material, the support plate is formed of a flexible material and/or the throughport is formed of a flexible material.

There is also disclosed a flexible port seal for insertion through tissue including an outer seal having a proximal end and a distal end. The outer seal is formed of a flexible material and defines a bore extending from the proximal end of the outer seal to the distal end of the outer seal. A support plate is integrally formed therewith of the flexible material and is located within the bore of the outer seal. A plurality of throughports are provided, e.g., integrally formed therewith, and may extend through the support plate and define throughbores for receipt of cannulas and/or surgical instruments therethrough.

In an embodiment, instrument seals are formed within each of the throughports such that the instrument seals form fluid tight seals against surgical instruments inserted through the throughbores of the throughports. In one specific embodiment, the instrument seals are hourglass seals. In an alternative specific embodiment, the instrument seals are duckbill valve type seals. Still further, the throughports may be hollow tubes without seals.

DESCRIPTION OF THE DRAWINGS

An embodiment of the presently disclosed flexible port seal is disclosed herein with reference to the drawings, wherein:

FIG. 1 is a perspective view of the disclosed flexible port seal;

FIG. 2 is a top view of the flexible port seal of FIG. 1;

FIG. 3 is a side view of the flexible port seal of FIG. 1 with a plurality of inner throughports and a support disk shown in phantom;

DETAILED DESCRIPTION

Figure 5:
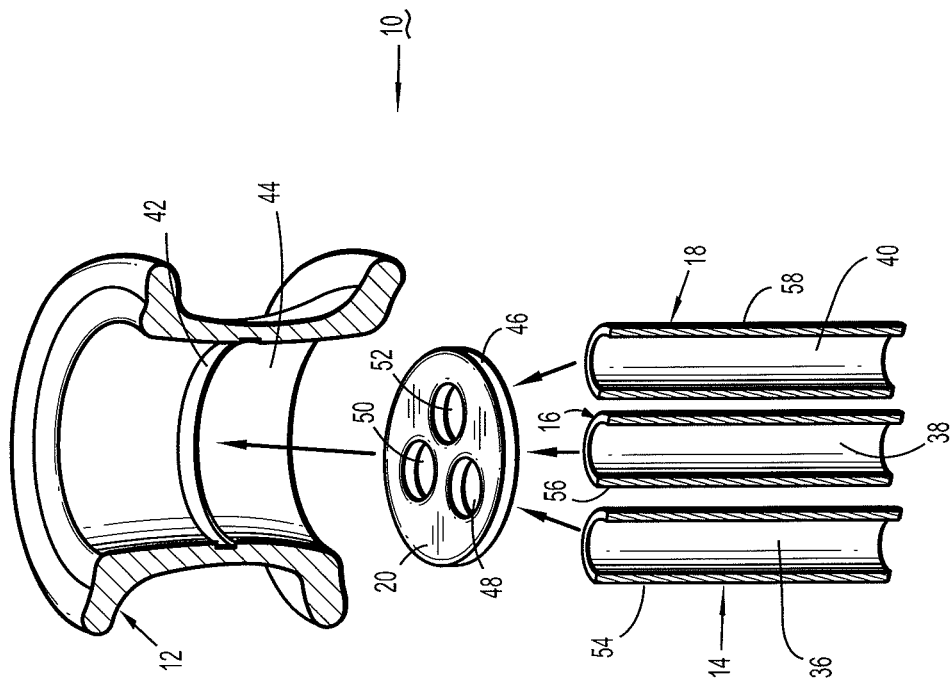
FIG. 5 is a perspective view, partially shown in section, of a flexible port seal with separable parts.

An embodiment of the presently disclosed flexible port seal will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Referring to FIGS. 1-3, there is disclosed a flexible port seal 10 for use in single incision surgery. Flexible port seal 10 is flexible or compressible to allow it to be inserted through a single incision in the body of a patient such that after insertion it will expand and seal within the incision. Additionally, the flexible nature of flexible port seal 10 allows surgical instruments inserted therethrough to be manipulated relative to their respective axes and thus allows a relatively high degree of movement of the surgical instruments to orient them appropriate to the tissue being operated upon.

Flexible port seal 10 generally includes an outer tissue seal 12 having one or more throughports 14, 16 and 18 extending therethrough. Throughports 14, 16 and 18 are provided to receive various surgical cannulas and/or instruments therethrough. The close proximity of throughports 14, 16 and 18 allows for unrestricted, independent movement of the surgical instruments inserted therethrough. As best shown in FIGS. 2 and 3, a central support plate or disk 20 is provided to support throughports 14, 16 and 18 within outer tissue seal 12.

Outer tissue seal 12 and central support disk 20 are formed from a flexible material which, as noted hereinabove, allows flexible port seal 10 to be compressed and inserted through an incision in the body of a patient as well as allowing for independent movement of throughports 14, 16 and 18 extending through support disk 20. Outer tissue seal 12 and support disk 20 may be formed of various materials such as, for example, silicone, thermoplastic elastomers, rubber, foam, gel, etc. Where desired, throughports 14, 16 and 18 may also be formed from various flexible materials and may be integrally formed therewith.

With continued reference to FIGS. 1-3, outer tissue seal 12 includes a central portion 22 having an upper rim 24 located at a proximal end 26 of central portion 22. A lower rim 28 is located on a distal end 30 of central portion 22. Upper rim 24 and lower rim 28 aid in preventing movement of flexible port seal 10 longitudinally through the incision in the patient.

With specific reference to FIG. 3, throughports 14, 16 and 18 may be attached to, e.g., integrally formed with and/or extend through, outer tissue seal 12 from a proximal end 32 of outer tissue seal 12 to a distal end 34 of outer tissue seal 12. It should be recognized that throughports 14, 16 and 18 may have different lengths as compared to each other, and may respectively extend in either direction for any distance relative to the support disk 20. For example, any one or more of the throughports 14, 16, 18 may extend beyond the proximal end 32 of outer tissue seal 12 or may extend to less than the proximal end 32 of the outer tissue seal 12, e.g., including not extending at all from the support disk 20. Also, any one or more of the throughports 14, 16, 18 may extend beyond the distal end 34 of outer tissue seal 12 or may extend to less than the distal end 34 of the outer tissue seal 12, e.g., including not extending at all from the support disk 20. These differences in lengths may allow the flexible port seal 10 to be more easily compressed prior to insertion within an incision. Furthermore, these differences in lengths may allow the flexible port seal 10 to accommodate different types of surgical instrumentation, different surgical procedures, etc.

Referring back to FIG. 2, throughports 14, 16 and 18 include respective throughbores 36, 38 and 40 for receipt of surgical cannulas and/or instruments in a manner described in more detail hereinbelow.

Figure 4:
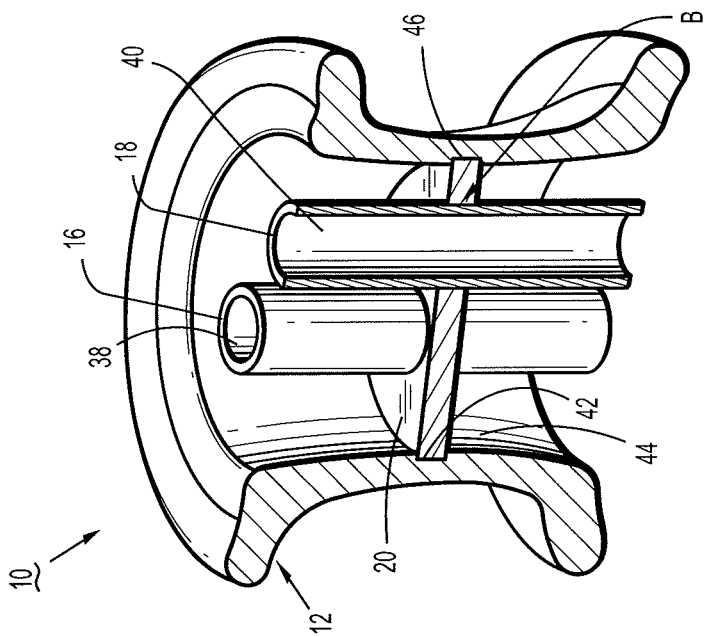
FIG. 4 is a perspective view, partially shown in section, of the flexible port seal of FIG. 1.

Referring now to FIGS. 4 and 5, as noted hereinabove central support disk 20 is provided within outer tissue seal 12 to support throughports 14, 16, and 18, within outer tissue seal 12. Central support disk 20 may be formed integrally with outer tissue seal 12 or may be provided as a separate component. When provided as a separate component, a groove 42 may be formed about an inner surface 44 of central portion 22 of central support disk 20. Alternatively, groove 42 may be provided at other locations within outer tissue seal 12. Upon assembly, a circumferential edge 46 of central support disk 20 fits within groove 42 by any type of mechanical connection, e.g., in friction fit fashion, such that circumferential edge 46 forms a fluid tight seal within groove 42.

In an embodiment, central support disk 20 is provided with a plurality of holes 48, 50 and 52 for receipt of throughports 14, 16 and 18, respectively. When positioned therethrough, outer surfaces 54, 56 and 58 of throughports 14, 16 and 18, respectively, foam fluid tight seals with holes 48, 50 and 52. It should also be noted that, due to the flexible nature of central support disk 20 and relatively small longitudinal contact area of central support disk 20 with throughports 14, 16 and 18, throughports 14, 16 and 18 are free to flex relative to central support disk 20 to allow for independent movement of surgical cannulas and/or instruments inserted through throughports 14, 16 and 18 in a manner described in more detail hereinbelow.

Figure 6:
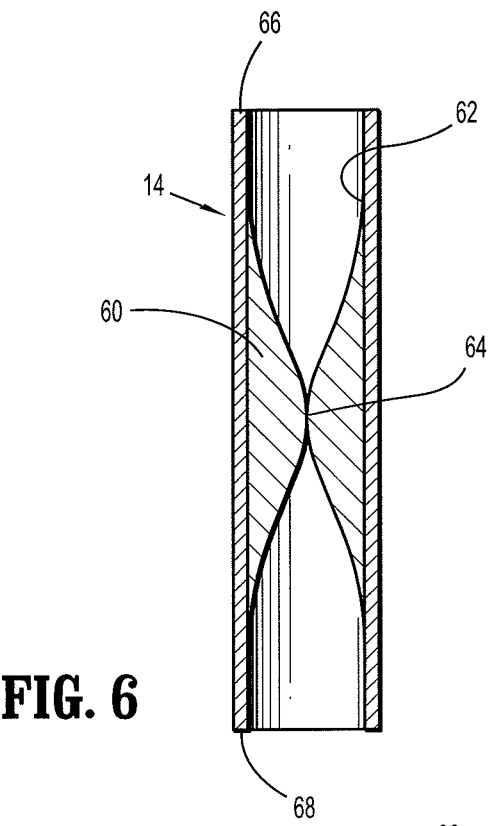
FIG. 6 is a side view, shown in section, of one embodiment of an inner throughport.
Figure 7:
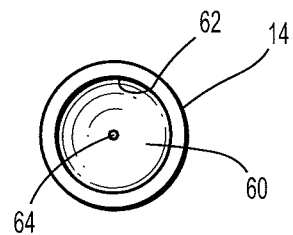
FIG. 7 is a top view of the inner throughport of FIG. 6.

Referring now to FIGS. 6 and 7, there is shown an embodiment in which the throughports 14, 16 and 18 are configured to seal directly with an instrument inserted therein, e.g., without the need for a cannula to be inserted first. In this embodiment, in order to provide a fluid tight seal between throughports 14, 16 and 18, for example throughport 14 shown here, and a surgical instrument inserted therethrough, throughport 14 is provided with an internal instrument seal. In this embodiment, the disclosed instrument seal is an hourglass type valve or seal 60 formed on an inner surface 62 of throughport 14 and defining a central opening or passageway 64 for receipt of a surgical instrument therethrough. Thus, as a surgical instrument is inserted through a proximal end 66 of throughport 14 it passes through and seals within central opening 64 and extends out of a distal end 68 of throughport 14.

Figure 8:
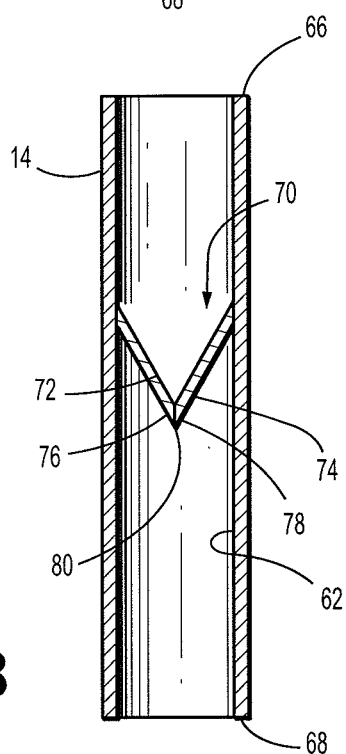
FIG. 8 is a side view, shown in section, of an alternative embodiment of an inner throughport.
Figure 9:
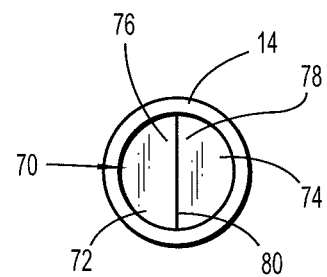
FIG. 9 is a top view of the inner throughport of FIG. 8.

Likewise, referring to FIGS. 8 and 9, in an alternative embodiment, the instrument seal provided within throughport 14 is a duckbill valve type seal 70 having a pair of flaps 72 and 74 extending from inner surface 62 of throughport 14. Distal ends 76 and 78 of flaps 72 and 74, respectively, define a slot 80 therebetween for sealing receipt of a surgical instrument there through. Similar to hourglass seal 60 described hereinabove, once a surgical instrument is inserted into proximal end 66 of throughport 14 it passes through and seals within slot 80 and extends out of distal end 68 of throughport 14.

It should be noted that, while the disclosed instrument seals formed within throughport 14 have been illustrated as an hourglass seal 60 (FIGS. 6 and 7) or a duckbill valve type seal 70 (FIGS. 8 and 9), other types of seals may be provided within throughports 14, 16 and 18 to seal about surgical instruments inserted therethrough. Furthermore, depending upon the nature of the surgical instruments to be used through throughports 14, 16 and 18, the instrument seals provided within throughports 14, 16, and 18 need not be identical and, in certain circumstances, may differ from each other.

Figure 10:
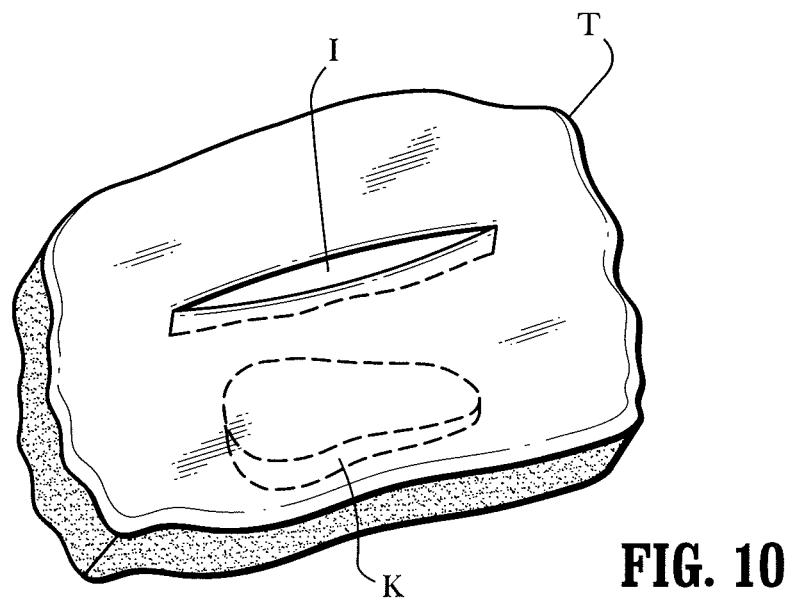
FIG. 10 is a perspective view of a tissue section having an incision therethrough with an underlying body organ shown in phantom.
Figure 11:
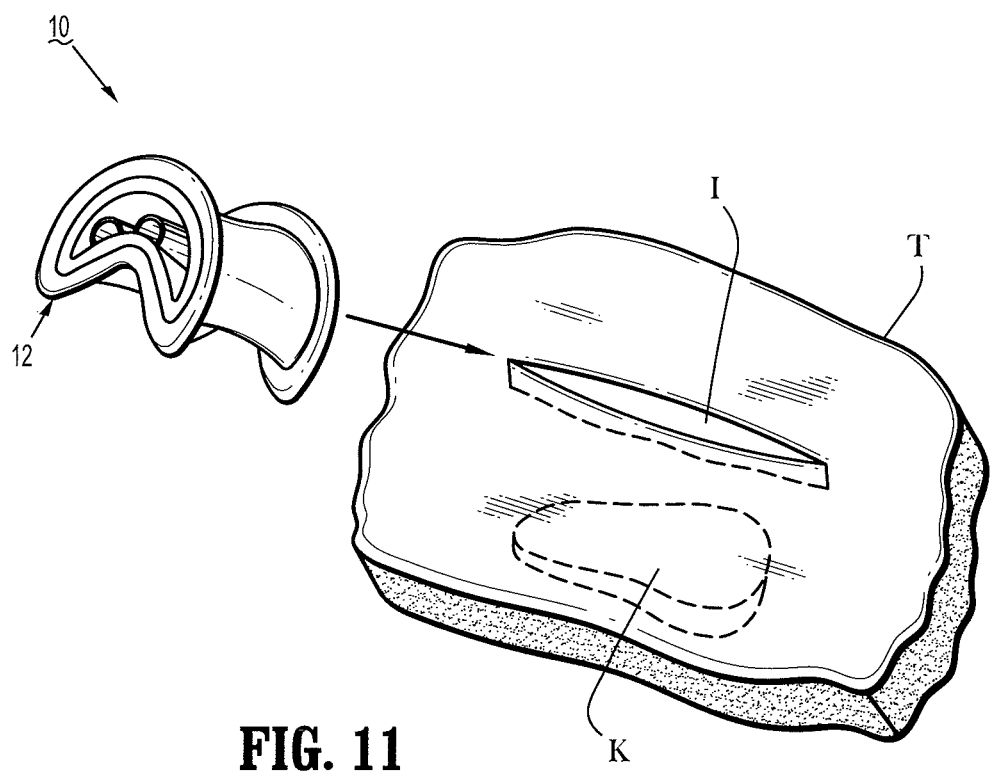
FIG. 11 is a perspective view of the flexible port seal of FIG. 1 prepared for insertion through the incision in the tissue.

Referring now to FIGS. 10-15, and initially with regard to FIGS. 10 and 11, the use of flexible port seal 10 in a single incision surgical procedure to perform a surgical procedure will now be described. The procedure discussed hereinbelow may be any type of surgical procedure, and is described as a procedure to excise and remove a body organ for illustrative purposes only. Initially, a single incision I is formed through a body tissue T and above a body organ, such as, for example, kidney K. In this surgical procedure it is desirable to operate on, and remove, kidney K with multiple surgical instruments while forming only a single incision I through body tissue T. With specific reference to FIG. 11, once incision I has been foamed through body tissue T, flexible port seal 10 may be squeezed or compressed to reduce it to a relatively smaller diameter for insertion through incision I. As noted hereinabove, outer tissue seal 12 is formed of flexible material which allows flexible port seal 10 to be compressed.

Figure 12:
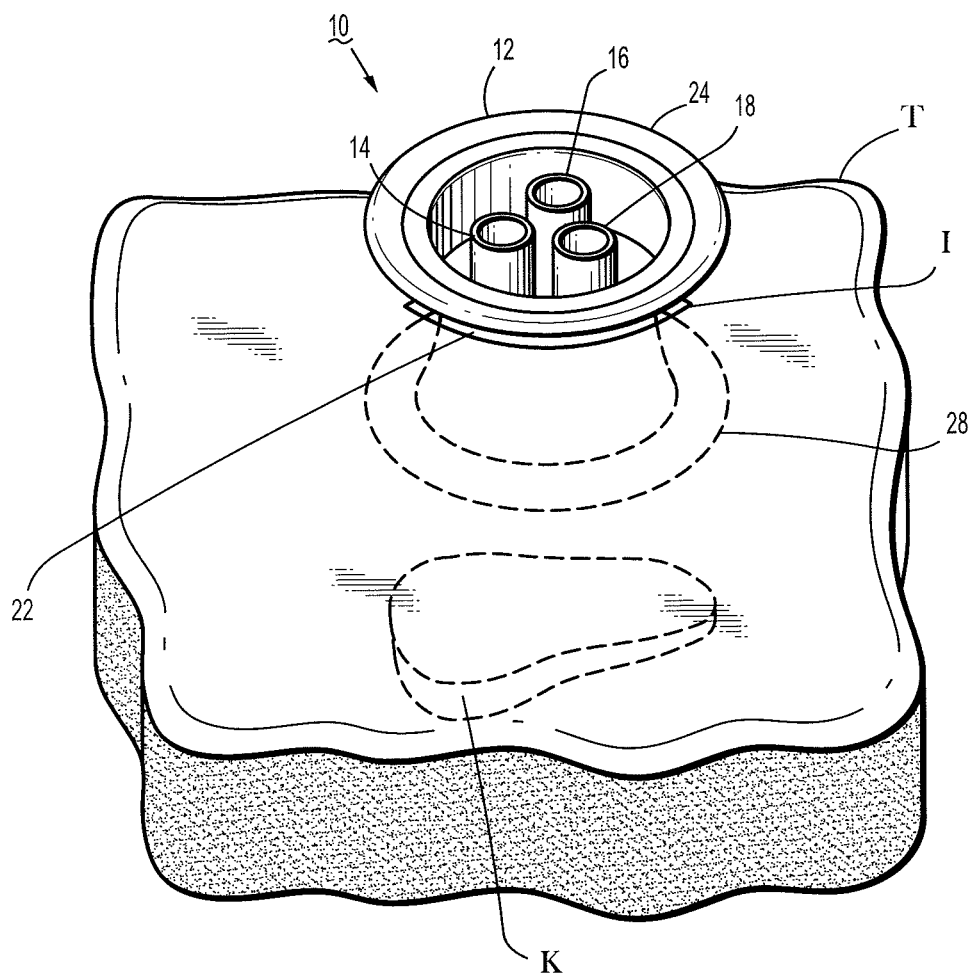
FIG. 12 is a perspective view of the flexible port seal of FIG. 1 positioned through the incision in the tissue.

Referring to FIG. 12, once flexible port seal 10 has been inserted through incision I pressure on the outer tissue seal 12 can be released allowing outer tissue seal 12 to return to its initial uncompressed state within incision I. As noted hereinabove, outer tissue seal 12 includes upper rim 24 and lower rim 28. Upper and lower rims 24 and 28, respectively, are provided to prevent migration of flexible port seal 10 through incision I in body tissue T. Once flexible port seal 10 has been positioned above kidney K, various surgical instruments may be inserted through throughports 14, 16 and 18 to operate on kidney K.

Figure 13:
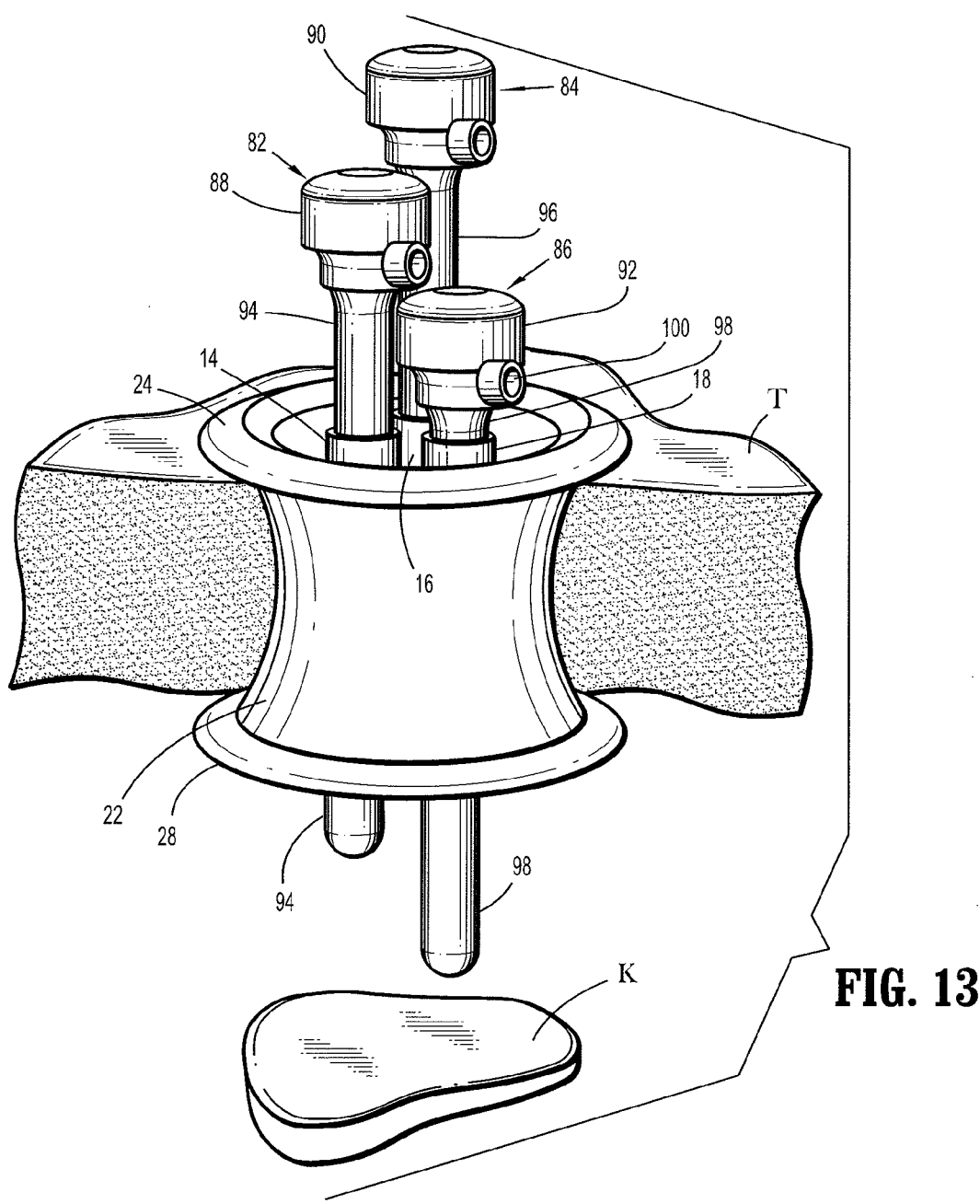
FIG. 13 is a side view, partially shown in section, of the flexible port seal of FIG. 1, with cannula ports and surgical instruments inserted therethrough and positioned above the body organ.

With specific reference to FIG. 13, as shown, surgical instrumentation, such as, for example, conventional cannulas 82, 84 and 86 may be inserted through throughports 14, 16 and 18. Cannulas 82, 84 and 86 include respective housings 88, 90 and 92. Housings 88, 90 and 92 include respective access tubes 94, 96 and 98 extending distally from housings 88, 90 and 92. With reference to cannula 86, for example, housing 92 of cannula 86 may be provided with an insufflation port 100 which is connected to a source of insufflation fluid to insufflate the area and within the body beneath tissue T and about kidney K. Alternatively, the flexible port seal 10 may have additional tubes, ports or connections (not shown) that separately operate to connect to and provide insufflation fluid or to provide smoke evacuation if desired. Once the body has been properly insufflated, kidney K may be operated upon to excise it from the surrounding tissue.

Figure 14:
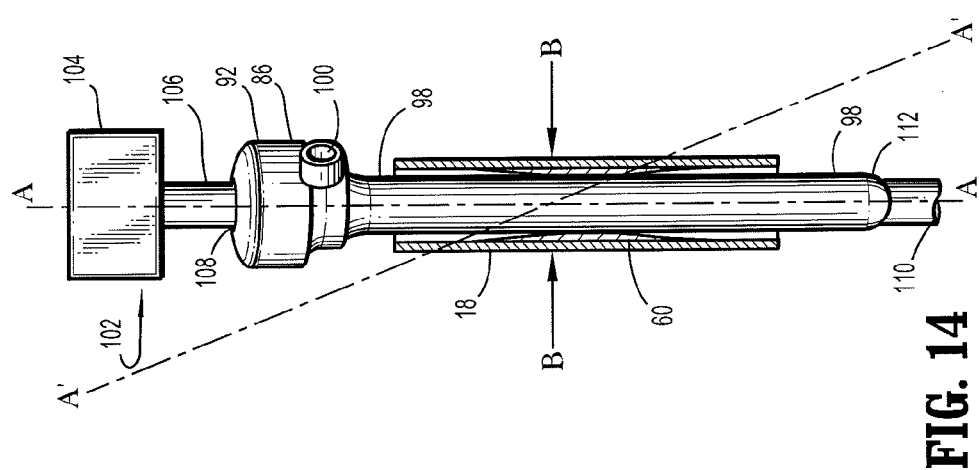
FIG. 14 is a side view, partially shown in section, of an inner throughport with a cannula and surgical instrument inserted therethrough.

Referring for the moment to FIG. 14, throughport 18 is illustrated with cannula 86 inserted therethrough. Specifically, access tube 98 is inserted through throughport 18. As illustrated, throughport 18 is provided with an instrument seal, such as, for example hourglass seal 60 which forms a fluid tight seal around access tube 98 inserted therethrough. Alternatively, the cannula 86 may be selected so as to have a tight fit within the throughbore of the throughport 18, thereby eliminating the need to have an instrument seal within the throughbore of the throughport 18. Also, the cannula 86 may include any type of fixation element, e.g., external threads, ribs, locking mechanisms, etc., that help maintain the cannula in position and help maintain the seal between the surface of the cannula 86 and the inner surface of the throughport 18.

Once cannula 86 has been properly inserted through throughport 18, a surgical instrument 102 may be inserted through cannula 86 to perform surgical operations on underlying tissue. Surgical instrument 102 includes a handle 104 having an elongate tubular member 106 extending distally from handle 104. Specifically, elongate tubular member 106 is inserted through a proximal opening 108 in housing 92 of cannula 86 such that a distal end of 110 of elongate tubular member 106 projects from a distal end 112 of access tube 98 of cannula 86. In this manner surgical instrument 102 may be positioned within the body to perform surgical operations on underlying tissue.

As noted hereinabove, central support disk 20 (FIG. 4) forms a fluid tight seal about throughport 18 at a relatively small contact area B with throughport 18. As shown in FIG. 14, throughport 18 defines a longitudinal axis A-A which coincides with the longitudinal axes of cannula 86 and surgical instrument 102 inserted therethrough. Due to the flexible nature of the throughport 18 and/or central support disk 20, throughport 18 may be flexed off-axis by manipulation of surgical instrument 102 and/or cannula 86 to reorient surgical instrument 102 along a flexed or offset axis A'-A'. This allows the surgeon to manipulate or orient surgical instrument 102 at various locations relative to the tissue being operated upon.

Figure 15:
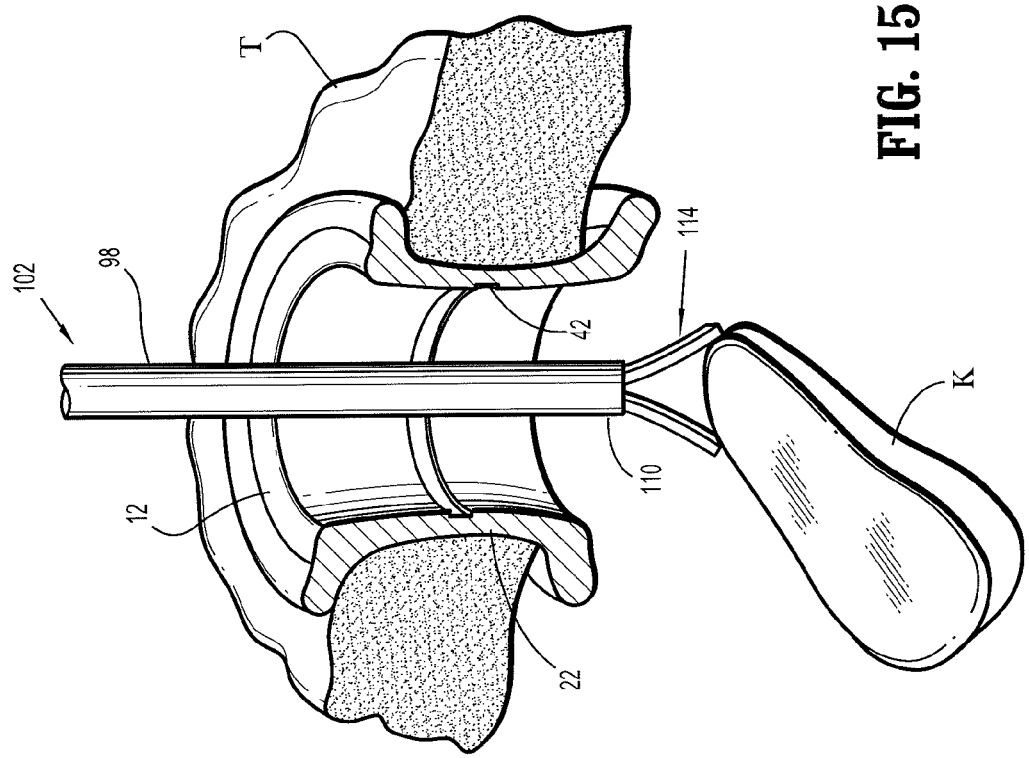
FIG. 15 is a side view, partially shown in section, of an outer seal of the flexible port seal positioned through the tissue and a surgical instrument positioned to perform a surgical procedure, according to an embodiment.

Referring now to FIG. 15, once surgical instrument 102 has been utilized to operate on underlying kidney K to excise or sever kidney K for harvesting, cannulas 80 to 84 and 86 may be removed from flexible port seal 10 and flexible port seal 10 withdrawn from incision I. Thereafter, a separate surgical instrument may be utilized to remove the excised kidney K from the body. Alternatively, where outer tissue seal 12 and central support disk 20 are formed as separate components, central support disk 20 can be removed from within outer tissue seal 12 leaving outer tissue seal 12 extending through incision I. In this situation, outer tissue seal 12 functions as a relatively large access port through tissue T. A surgical instrument, such as, for example, surgical instrument 102, may be inserted through outer tissue seal 12 and manipulated such that an end effector 114, positioned on distal end 110 of access tube 98, is utilized to grasp kidney K and withdraw kidney K from within the body and through outer tissue seal 12. Alternatively, the entire flexible port seal 10 may be removed from the incision prior to withdrawing the kidney K through the incision.

Once kidney K has been removed from the body, the single incision I can be closed in a conventional manner. Thus, flexible port seal 10 provides multiple, independently movable instrument access ports through a single incision in the patient's body.

It will be understood that various modifications may be made to the embodiments disclosed herein. For example, as noted hereinabove, the disclosed throughports may also be formed of flexible materials to allow for the use of articulating surgical instruments therethrough. Further, the disclosed flexible port seal may be provided with multiple throughports in excess of the disclosed three throughports. Additionally, the lengths and diameters of the disclosed throughports need not be identical but may be varied depending upon the contemplated surgical instrumentation to be utilized therethrough. Still further, the throughports need not be straight as shown, but any one or more may be curved, bent, or have any other shape suitable to receive a particular surgical instrument. Also, while the support disk is shown as being relatively straight, thin and having a relatively constant thickness, the support disk may be curved or contoured, may be thicker if desired and/or may have varying thicknesses over its area, e.g., to improve its flexibility, to improve its sealing capabilities, to improve its resistance to tearing when manipulated. In addition, while the support disk is shown as being located at approximately a longitudinal midpoint of the flexible port seal, it may instead be located at any location between the proximal and distal ends of the flexible port seal. Therefore, the above description should not be construed as limiting, but merely as exemplifications of particular embodiments. Those skilled in the art will envision other modifications within the scope and spirit of the claims appended hereto.

The invention claimed is:

1. A flexible port seal for insertion through tissue comprising:
   an outer seal defining a bore extending from a proximal end of the outer seal to a distal end of the outer seal, along a central longitudinal axis;
   a support plate located within the bore of the outer seal, the entire flexible port seal transitionable between an expanded state and a compressed state to facilitate insertion of the flexible port seal through tissue; and
   a throughport defining a throughbore for receipt of a surgical instrument, the throughport extending through the support plate and longitudinally adjustable through the support plate, the throughport disposed entirely within the bore of the outer seal and extending between the proximal and distal ends of the outer seal, wherein the throughport forms a fluid tight seal against a surgical instrument inserted through the throughport, wherein the outer seal has a groove formed in an inner surface of the outer seal for receipt of the support plate, wherein in the compressed state the entire flexible port seal is squeezed or compressed inwards towards the central longitudinal axis to reduce the flexible port seal to a relatively smaller diameter for insertion through an incision.

2. The flexible port seal as recited in claim 1, wherein the outer seal has a central portion and an upper rim at a proximal end of the central portion.

3. The flexible port seal as recited in claim 2, wherein the outer seal has a lower rim at a distal end of the central portion.

4. The flexible port seal as recited in claim 2, wherein the upper rim has a diameter greater than a diameter of the central portion.

5. The flexible port seal as recited in claim 1, wherein the support plate is a circular disk.

6. The flexible port seal as recited in claim 1, wherein the throughport is a hollow tube attached to the support plate.

7. The flexible port seal as recited in claim 6, wherein the throughport includes an instrument seal located within a bore of the hollow tube.

8. The flexible port seal as recited in claim 7, wherein the instrument seal is an hourglass seal.

9. The flexible port seal as recited in claim 7, wherein the instrument seal is a duckbill valve.

10. The flexible port seal as recited in claim 1, wherein the outer seal is formed of a flexible material.

11. The flexible port seal as recited in claim 1, wherein the support plate is formed of a flexible material.

12. The flexible port seal as recited in claim 1, further comprising one or more additional throughports.

13. The flexible port seal as recited in claim 1, further comprising one or more of throughports, the one or more of throughports being straight.

14. The flexible port seal as recited in claim 13, wherein the one or more of throughports have varying lengths.

15. The flexible port seal as recited in claim 3, wherein proximal and distal ends of the throughport are located between the upper rim and the lower rim.

16. The flexible port seal as recited in claim 1, wherein the throughport is removably coupled to the support plate.

17. The flexible port seal as recited in claim 13, wherein the one or more throughports is movable independent of each other.

18. The flexible port seal as recited in claim 1, wherein the throughport is pivotable with respect to the support plate.

19. The flexible port seal as recited in claim 1, wherein the support plate is made of a foam material.

* * * * *